US010092666B2

(12) United States Patent
Quagliarella et al.

(10) Patent No.: US 10,092,666 B2
(45) Date of Patent: Oct. 9, 2018

(54) AIR FILTER UNIT

(71) Applicant: SIDEL PARTICIPATIONS S.A.S., Octeville-sur-Mer (FR)

(72) Inventors: Pierluigi Quagliarella, Parma (IT); Rossana Borgese, Parma (IT)

(73) Assignee: SIDEL PARTICIPATION S.A.S., Octeville-sur-Mer (FR)

( * ) Notice: Subject to any disclaimer, the term of this patent is extended or adjusted under 35 U.S.C. 154(b) by 343 days.

(21) Appl. No.: 14/956,887

(22) Filed: Dec. 2, 2015

(65) Prior Publication Data
US 2016/0175468 A1 Jun. 23, 2016

(30) Foreign Application Priority Data
Dec. 19, 2014 (EP) .................................. 14199516

(51) Int. Cl.
*A61L 2/16* (2006.01)
*A61L 9/015* (2006.01)
(Continued)

(52) U.S. Cl.
CPC ........ *A61L 2/16* (2013.01); *A61L 9/14* (2013.01); *B01D 46/0023* (2013.01);
(Continued)

(58) Field of Classification Search
None
See application file for complete search history.

(56) References Cited

U.S. PATENT DOCUMENTS 4,742,764 A * 5/1988 Duvlis ...................... F24F 9/00
454/190
5,922,095 A * 7/1999 Hustvedt ................ B01D 45/06
454/187
(Continued)

FOREIGN PATENT DOCUMENTS

DE 102004027354 A1 2/2006
EP 0815919 A2 1/1998
(Continued)

OTHER PUBLICATIONS

Extended European Search Report dated Jun. 1, 2015 by the European Patent Office in counterpart European Patent Application No. 14199516.7.

*Primary Examiner* — Amber R Orlando
*Assistant Examiner* — Brit E. Anbacht
(74) *Attorney, Agent, or Firm* — Finnegan, Henderson, Farabow, Garrett & Dunner LLP (57) ABSTRACT

An air filter unit for removing contaminations from air is disclosed. The air filter unit includes an airflow generating device configured to generate and direct at least one airflow from an air inlet to an air outlet, a filter disposed between the air inlet and the air outlet and including at least one filter layer for removing contaminations from the at least one airflow, a heater disposed upstream of the filter and configured to heat the at least one airflow directed towards the filter, an ejection device disposed upstream of the filter and configured to inject a sterilizing agent into the at least one airflow directed towards the filter, and a duct interposed between the air inlet and the filter and configured to feed the at least one airflow to the filter. The duct includes a volute-like outlet portion, and the ejection device is arranged in the duct.

22 Claims, 3 Drawing Sheets

(51) Int. Cl.
  *A61L 9/14* (2006.01)
  *B01D 46/00* (2006.01)
  *B01D 46/12* (2006.01)
  *B01D 46/42* (2006.01)

(52) U.S. Cl.
  CPC ..... *B01D 46/0028* (2013.01); *B01D 46/0041* (2013.01); *B01D 46/12* (2013.01); *B01D 46/4263* (2013.01); *A61L 9/015* (2013.01); *A61L 2209/14* (2013.01); *A61L 2209/211* (2013.01); *B01D 2273/30* (2013.01); *B01D 2279/65* (2013.01)

(56) References Cited

U.S. PATENT DOCUMENTS

| | | | |
|---|---|---|---|
| 8,449,829 B2* | 5/2013 | Nagatani | A61L 2/208 422/120 |
| 2004/0139858 A1* | 7/2004 | Entezarian | B01D 46/30 95/275 |
| 2009/0169421 A1 | 7/2009 | Nagatani et al. | |
| 2015/0114822 A1* | 4/2015 | Greco | B01D 53/007 204/158.21 |

FOREIGN PATENT DOCUMENTS

| | | |
|---|---|---|
| EP | 2049227 | 4/2009 |
| JP | H11 105832 A | 4/1999 |

\* cited by examiner

AIR FILTER UNIT

CROSS-REFERENCE TO RELATED APPLICATIONS

This application claims the benefit of priority of European Patent Application No. 14199516.7, filed on Dec. 19, 2014, which is incorporated herein by reference.

TECHNICAL FIELD

The present invention relates to an air filter unit for removing contaminations from an airflow directed into a clean/sterile environment, such as an aseptic working environment.

BACKGROUND

Filter units are generally used for cleaning air from macroscopic and microscopic contaminations such as dust, microbes and viruses. An airflow is directed through the filter unit in such a way that undesired contaminations are retained by the filter unit and sterile air containing a reduced number of contaminations or no contaminations at all exits the filter unit and is directed into clean/aseptic/sterile working environment or a clean room requiring sterile air.

Filter units for supplying sterile air to sterile working environments are commonly used in medical facilities or in automotive, electronic, pharmaceutical and biotechnology industries or even in the food packaging industry, just to name a few.

Filter units exist in a large variety of solutions and new developments are ongoing in order to improve the quality of the filter units themselves, and, accordingly, to improve the quality and the sterility of the air exiting the filter units.

Filter units are known which comprise one single High-Efficiency Particulate it (HEPA) filter layer or one single Ultra-Low Particulate Air (ULPA) filter layer. These solutions are commonly used for the most stringent applications, including e.g. applications in the food packaging industry, in particular for allowing aseptic production conditions, where sterile working environments are required to increase shelf-life stability of the packaged product and, consequently, consumer safety.

Recently, filter units comprising at least two filter layers have been developed to increase filter efficiency and to guarantee that, even in the event of damage of one filter layer, the air entering the clean/sterile working environment is sterile. This is now one of the requirements laid down by FDA for sterile working environments in the food industry.

It has to be considered that from time to time the filter units need to be sterilized themselves in order to devitalize contaminants such as microbes, viruses and spores filtered out of the air by the filter layers and trapped in these filter layers so that the required quality of the filter units and their respective filter efficiencies can be re-established. Therefore, the design of filter units also needs to consider adequate and efficient means and ways of sterilization.

An example of a known air filter unit comprising respective sterilization means is described in EP2049227. This filter unit comprises a blower configured to direct an airflow, heated by an integrated heating device, through two filter layers; the filter unit further comprises a sterilization layer, which is interposed between the two filter layers and in which liquid or vaporous hydrogen peroxide ($H_2O_2$) can be injected to sterilize the filter unit. A pre-filter is also provided at an air inlet to filter out larger contaminations from the airflow entering the unit. During the sterilization of the filter unit, the two filter layers are saturated with liquid or vaporous hydrogen peroxide injected through the sterilization layer and the heating device and the blower are activated. Thus, an airflow is generated through the two filter layers.

The heating device heats the airflow to a temperature above, the activation temperature of the hydrogen peroxide, so that the hydrogen peroxide degrades and reacts on contaminations such as microbes, viruses and spores. Eventually, the blower and the heating device are deactivated once the degradation and, thus, the reaction on the contaminations of the hydrogen peroxide has been initiated. After the sterilization reactions have been terminated, the filter layers can be dried by activating again the blower and the heating device. At the very end, the blower can be activated to remove the degradation products from the filter unit.

Another example of a known air filter unit, in particular for supplying clean/sterile air to a work environment in a food packing factory, is disclosed in US 2009/169421.

This filter unit comprises:
a blower configured to generate and direct en airflow from an air inlet to an air outlet;
a pre-filter arranged at the air inlet for filtering out macroscopic contaminations, such as larger diameter dust, from the airflow entering the filter unit;
two filter layers oriented perpendicularly to each other and through which the airflow coming from the pre-filter passes prior to enter the clean/sterile working environment;
a heater arranged between the blower and the two filters and adapted to adjust the temperature and the humidity of the airflow; and
a chemical gas agent eject apparatus configured to inject gaseous hydrogen peroxide into the airflow upstream of the two filters and downstream of the heater.

In the example embodiment described in US 2009/169421, the first filter layer crossed by the airflow includes a HEPA filter, whilst the other filter layer includes an ULPA filter.

The operation of the filter unit shown in US 2009/169421 is similar to that described with reference to the filter unit of EP2049227. Even in this case, during sterilization, hydrogen peroxide is supplied through the chemical gas agent eject apparatus into the airflow, which is simultaneously heated to a given temperature.

Air filter units of the type described above are used widely and satisfactorily to supply cleaned/sterilized air to clean/sterile working environments. Within the industry, however, of demand for further improvements is felt, particularly in view of the continual request to increase the filter performance as well as the sterilization efficiency and reliability of the known air filter units.

BRIEF SUMMARY

It is therefore an object of the present invention to provide an air filter unit, which allows to satisfy the aforementioned, demand typically associated with known filter units.

According to the present invention, there is provided an air filter unit as claimed in claim 1.

BRIEF DESCRIPTION OF THE DRAWINGS

A preferred, non-limiting embodiment of the present invention will be described by way of example with reference to the accompanying drawings, in which.

DETAILED DESCRIPTION

Figure 1:
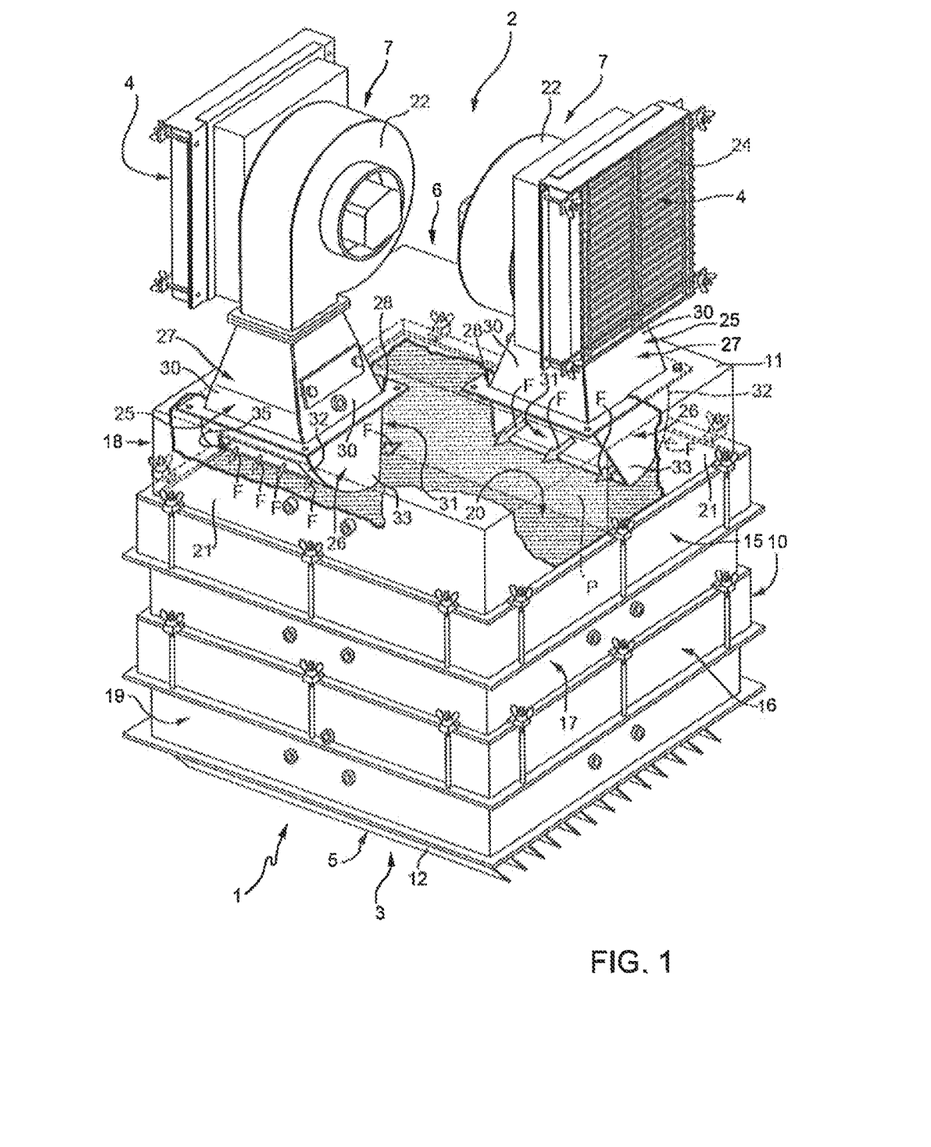
FIG. 1 shows a perspective view of an air filter unit according to the present invention, with parts removed for clarity.

Number 1 in FIG. 1 indicates as a whole an air filter unit adapted to clean air, i.e. to remove contaminants from the air. The unit 1 is adapted to be placed at the boundary between an untreated environment 2 and a clean/sterile environment 3 in order to direct sterilized air into this latter environment.

In particular, unit 1 is adapted to generate and direct at least one airflow F from a respective air inlet 4, connected to the untreated environment 2, to an air outlet 5, connected to the clean/sterile environment 3.

In the example shown, unit 1 is adapted to generate two distinct airflows F, each one directed from a respective air inlet 4 to the same common air outlet 5.

Figure 2:
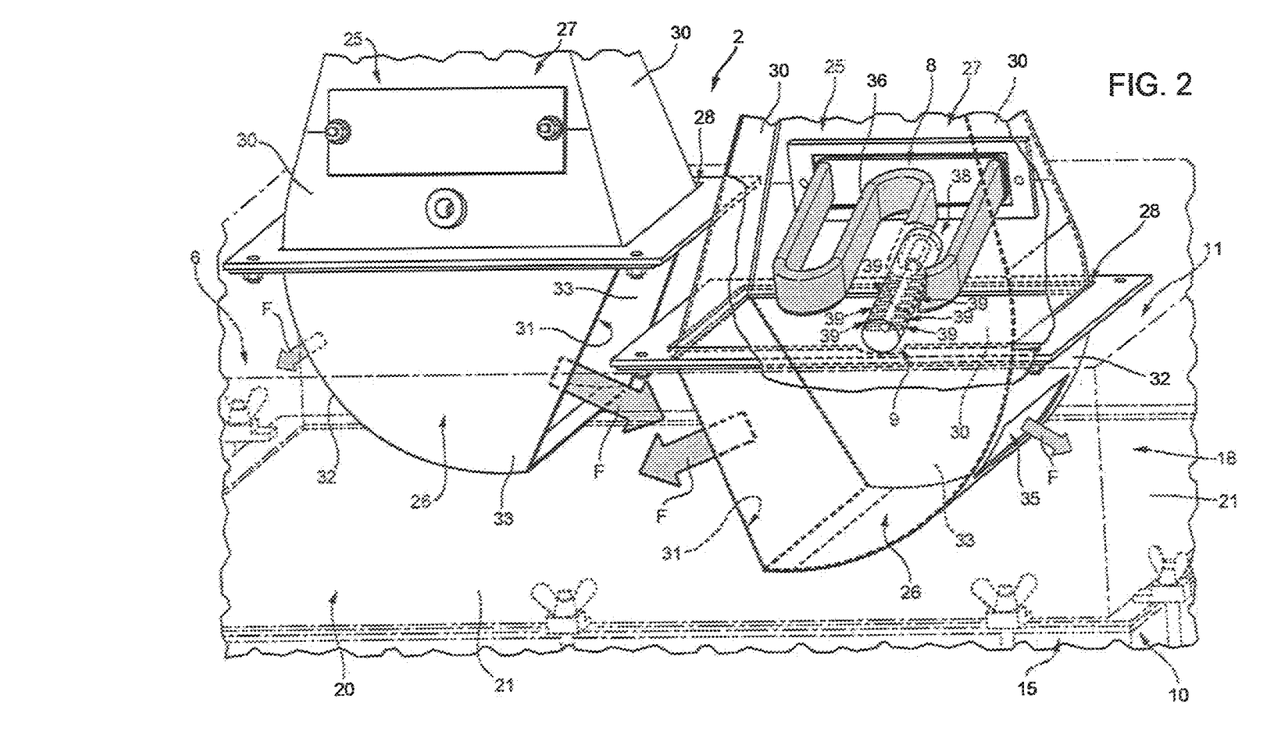
FIG. 2 shows a larger-scale perspective view, taken from a different direction, of a detail of FIG. 1, with parts removed for clarity.
Figure 3:
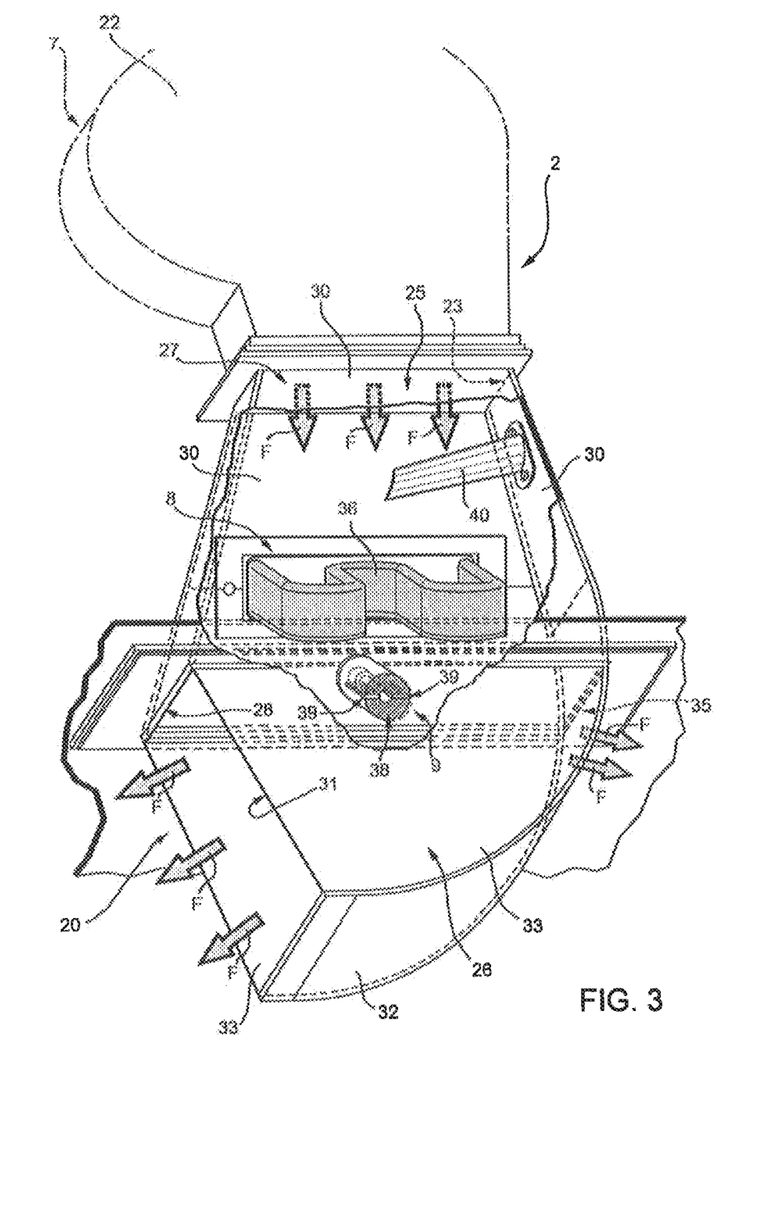
FIG. 3 shows a larger-scale perspective view, taken from the same direction as FIG. 2, of another detail of FIG. 1, with parts removed for clarity.

With reference to FIGS. 1 to 3, unit 1 comprises:
- a filter assembly 6 arranged between air inlets 4 on one side and air outlet. 5 on the opposite side;
- two airflow generating devices 7, preferably disposed upstream of filter assembly 6 and adapted to generate airflows F from the respective air inlets 4 to air outlet 5;
- heating means 8 for heating the airflows F before they pass through filter assembly 6; and
- ejection means 9 adapted to inject vaporized, gaseous or liquid sterilizing agent, in particular hydrogen peroxide, into airflows F directed towards the filter assembly 6.

With reference to FIG. 1, filter assembly 6 comprises a box-like structure 10, preferably having a parallelepiped configuration; box-like structure 10 is delimited, at one end, by air outlet 5, and at its opposite end, by a wall 11 supporting airflow generating devices 7. As visible in FIG. 1, air outlet 5 is positioned at the bottom of box-like structure 10 and is covered by a grid 12 (only partially visible in FIG. 1) for protection purposes against aggressive chemical sterilizing treatment of the filter unit 1, whilst wall 11 is positioned at the top of the same structure.

Filter assembly 6 comprises:
- a first filter layer 15 interposed between airflow generating devices 7 and air outlet 5, and therefore between air inlets 4 on one side and the air outlet 5 on the opposite side;
- a second filter layer 16 extending parallel to filter layer 15 and interposed between the latter and air outlet 5; and
- a hollow spacer 17 separating filter layers 15 and 16 so as to create an air cap therebetween.

Filter layers 15 and 16 are both plate-shaped and extend parallel to wall 11.

It is pointed out that hollow spacer 17 may be made thinner than the one shown in FIG. 1 or even eliminated by putting the filter layers 15 and 16 in direct contact with one another. In this way, filter assembly 6 may be made more compact in a direction orthogonal to filter layers 15 and 16.

Filter assembly 6 also comprises two plate-shaped hollow bodies 18, 19, one (13) formed between wall 11 and filter layer 15, and the other one (19) located downstream of filter layer 16 with respect airflows F and defining air outlet 5.

Hollow body 18 defines a chamber 20, preferably of parallelepiped configuration, open towards filter layer 15 and delimited by wall 11 and a by a plurality of lateral walls 21, four in the example shown, protruding orthogonally from respective sides of the wall 11 itself; hollow body 18 creates an air gap between end wall 11 and filter layer 15 and is configured to receive airflows F from air-flow generating devices 7.

Hollow body 19 creates another air gap between filter layer 16 and air outlet 5. According to a possible alternative not shown, hollow body 19 may be eliminated in order to make filter assembly 6 more compact in a direction orthogonal to filter layers 15 and 16.

With reference to FIGS. 1 to 3, each air-flow generating device comprises a blower 22 adapted to aspirate air from untreated environment 2 through relative air inlet and to blow it to a blower outlet 23 in turn connected with chamber 20 of filter assembly 6; therefore, blower 22 is configured to generate a relative airflow F directed to cross filter assembly 6 and to reach clean/sterile environment 3 through air outlet 5.

Conveniently, a pre-filter 24 is mounted between each air inlet 4 and the relative blower 22 to remove macroscopic contaminations from the air entering the blower 22 itself.

As shown in FIG. 1, air inlets 4 lie on parallel planes orthogonal to filter layers 15, 16 and to the plane on which air outlet 5 lies. Blower outlet 23 lies on a plane parallel to the one of air outlet 5. In the example shown, air inlets 4 are vertically oriented, whilst air outlet 5 and blower outlet. 23 extend horizontally.

In the preferred embodiment described with reference to the enclosed Figures, air inlets 4, air outlet 5 and blower outlet 23 all have rectangular profiles.

Each blower 22 is connected to filter assembly 6 through a relative duct 25. In this way, each duct 25 is surmounted by respective blower 22.

With reference to FIGS. 1 to 3, heating means 8 and ejections means 9 are advantageously arranged within each duct 25, and this duct 25 comprises at least an outlet portion 26 having a volute-like configuration to increase mixing between the relative airflow F and the sterilizing agent injected within the duct 25 itself by ejection means 9.

The use of the volute-like outlet portion 26 for each duct 25 also permits a very uniform distribution of the heat to the relative airflow 5 and/or the mixture of air and sterilizing agent moving towards filter assembly 6.

According to a possible alternative not shown, heating means 8 may be also arranged upstream of the relative duct 25 with respect to the relative airflow F, for instance they may be integrated in the relative blower 22.

According to another possible alternative not shown, each duct 25 may be also entirely configured like a volute.

In the illustrated example, each duct 25 has an inlet portion 27 connecting the relative blower outlet 23 to a relative opening 28 formed in wall 11 of filter assembly; the inlet portion 27 of each duct 25 has an increasing section passing from the relative blower outlet 23 to the relative opening 28; in addition, each inlet portion 27 preferably has the shape of a truncated pyramid and is delimited by four lateral walls 30, each having substantially the profile of an isosceles trapezium.

Volute-like outlet portion 26 of each duct extends within chamber 20 and defines a main outlet opening 31 lying on a plane transversal to filter layers 15 and 16.

More specifically, main outlet opening 31 of each duct 25 lies on a plane slanted with respect to filter layer 15 and defining with the latter an acute angle; in this way the airflow F exiting from main outlet opening 31 of each duct 25 has a given inclination with respect to filter layer 15 smaller than 90° and includes a tangential component with respect to the filter layer 15 itself.

Outlet portions 26 of ducts 25 are arranged inside chamber 20 of hollow body 18 at opposite corners or sides thereof; more specifically, the outlet portions 26 of ducts 25 are mounted in the proximity of diagonally opposite respective corners of hollow body 18.

Outlet portion 26 of each duct 25 is delimited by a curved wall 32, having an arc-shaped lateral profile and facing one of the lateral walls 21 of hollow body 18, and by two parallel lateral walls 33 extending on the opposite sides of curved wall 32; lateral walls 33 and curved wall 32 extend on the prolongation of respective lateral walls 30 of the relative inlet portion 27.

In the example shown, curved walls 32 of ducts 25 face opposite lateral walls 21 of hollow body 18.

Main outlet opening 31 of each duct 25 is delimited by wall 11 and by the head edges of the relative curved wall 32 and lateral walls 33.

In order to increase turbulence of the air in chamber 20 and therefore a better heating and mixing of the air with the sterilizing agent prior to supplying the resulting mixture to filter layers 15 and 15, main outlet openings 31 of ducts 25 face respective staggered portions of an intermediate plane P extending between the ducts 25 themselves and orthogonal to wall 11 and filter layers 15 and 16.

Main outlet openings 31 of ducts 25 lie on respective slanted planes diverging from one another towards filter layers 15 and 16.

With reference to FIGS. 1 and 2, outlet portion 26 of each duct 25 further comprises an auxiliary outlet opening 35 formed in relative curved wall 32 and disposed opposite to the relative main outlet opening 31. Auxiliary outlet openings 35 allow parts of respective airflows F to reach corner areas of filter layers 15 and 16.

In the example shown, each auxiliary outlet opening 35 presents a smaller dimension than the respective main outlet opening 31.

With reference to FIGS. 2 and 3, heating means 8 comprise, for each airflow F, a serpentine heating member 36 projecting transversally within inlet portion 27 of the relative duct 25 from a lateral wall 30 thereof and adapted to heat the air coming from the relative blower 22 prior to reaching filter layers 15 and 16.

In particular, heating member 36 includes an electric resistance (know as such and not shown) and is inclined towards outlet portion 26 of the relative duct 25 and therefore towards filter layers 15 and 16.

This arrangement of heating member 36 within the relative duct 25 is aimed at achieving an uniform. heating of the relative airflow F.

With reference to FIGS. 2 and 3, ejection means 9 comprise, for each airflow F, an ejection conduit 38 projecting transversally within inlet portion 27 of the relative duct 25 from a lateral wall 30 thereof and provided with at least one radial outlet hole 39 having an axis transversal to the relative airflow F. In the example shown, each ejection conduit 38 is provided with two series of diametrically opposite radial outlet holes 39.

In particular, ejection conduit 38 is inclined towards outlet portion 26 of the relative duct 25 and therefore towards filter layers 15 and 16.

In addition, ejection conduit 38 extends from the same lateral wall 30 of the relative inlet portion 27 as heating member 36.

As shown in FIGS. 2 and 3, outlet holes 39 of each ejection conduit 38 preferably lie on a common plane extending transversally to the relative airflow F and defining an acute angle with wall 11 and therefore with filter layers 15 and 1, parallel to such wall 11.

The particular arrangement of each ejection conduit 38 within the relative duct 25 is aimed at increasing mixing of the sterilizing agent exiting from the outlet holes 39 with the relative airflow F.

Ejection conduit 38 is supplied with the vaporous, gaseous or liquid sterilizing agent by a sterilizing agent reservoir not shown and known as such.

Each heating member 36 and the corresponding election conduit 38 are disposed downstream of the relative blower outlet. 23 and upstream of filter layers 15, 16 with respect to the relative airflow F.

Furthermore, each heating member 36 and the corresponding election conduit 38 are arranged adjacent to one another. In particular, each ejection conduit 38 is disposed downstream of the corresponding heating member 36 with respect to the relative airflow F.

With reference to FIG. 3, each duct 25 is also internally provided with a deflector element 40 extending transversally to the relative airflow F and adapted to disrupt the latter in order to create a turbulent movement, of the air.

In particular, each deflector element 40 is arranged upstream of the relative heating member 36 and immediately downstream of the relative blower outlet 23.

Each deflector element 40 projects from one of lateral walls 30 of the inlet portion 27 of the relative duct 25.

In use, during normal working operation, blowers 22 aspirate air from untreated environment 2 and generate respective airflows F towards the clean/sterile environment 3. Pre-filters 24 filter out larger-sized contaminations from the air directed towards the inside of blowers 22.

The air exit blowers 22 at respective blower outlets 23 and progresses along respective ducts 25. The airflows F enter respective chambers 20 of hollow bodies 18 through volute-like outlet portions 26 of respective ducts 25.

The use of volute-like outlet portions 26 of ducts 25 along with the particular arrangement of such outlet portions 26 at opposite sides of chamber 20 with facing and staggered main outlet openings 31 produce a turbulence in the air within chamber 20. In practice, the air exiting from one of main outlet openings 31 flows against the air exiting from the other main outlet opening 31 increasing turbulence and mixing of the airflows F. The air then passes thereby through filter layers 15 and 16.

During passage through these filter layers 15, 16, contaminations not filtered out by pre-filter 24 are removed from the air flowing towards air outlet 5. Thus, cleaned/sterilized air exits from filter unit 1 and enters clean/sterile environment 3.

When unit 1 needs to be sterilized during a sterilization cycle, the function of the unit 1 is essentially identical to what is explained above. Additionally to the activation of blowers 22, also respective heating members 36 and respective ejection conduits 38 are activated. In particular, each heating member 36 heats the relative airflow, while each ejection conduit 38 receives the vaporous, gaseous or liquid sterilizing agent from the sterilizing agent reservoir and injects it through outlet holes 39 into heated air moving through the relative duct 25.

In particular, the sterilizing agent is injected in the ducts 25 transversally to the respective airflows F; this together with the turbulence of the air flowing in chamber 20 through the volute-like outlet, portions 26 produce a very deep mixing of the sterilizing agent with the heated air.

The mixture of air and sterilizing agent exits from each duct 25 through the opposite main and auxiliary outlet openings 31, 35, thereby reaching any corner of filter layers 15 and 16.

Thus, overall, the airflows F directed through filter layers 15, 16 contain a desired quantity of sterilizing agent which is activated by adjusting an adequate temperature of the air in such airflows by the heating members 36. The active sterilizing agent deactivates and decompose the contaminations leaving behind water and decomposition products.

At the end of the sterilization cycle election conduits 38 are deactivated. Heating members 36 are further maintained in an active condition until filter layers 15, 16 are dried out.

Finally, blowers 22 are activated to blow the decomposition products out of the unit alternatively, blowers 22 may be activated to work in a suction mode so as to remove the decomposition products from filter layers 15, 16 by suction.

The advantages of air filter unit 1 according to the present invention will be clear from the foregoing description.

In particular, air filter unit 1 presents, with respect to the known solutions previously described and discussed, an increased mixing effect and behavior of the sterilizing agent in the airflows due to:
- use of the volute-like outlet portion 26, which increases turbulence of the mixture formed by the air and the sterilizing agent;
- injection of the sterilizing agent transversally into the airflows;
- arrangement of the main outlet openings 31 of the two ducts 25 lying on respective planes transversal to filter layers 15, 16;
- arrangement of the volute-like outlet portions 26 of the two ducts 25 at spaced locations within, the chamber 20 and with their main outlet openings 31 facing an intermediate plane P there between so as to further increase turbulence of the air; and
- use of deflector elements 40 to disrupt the respective airflows F at the entry within ducts 25, thereby increasing turbulence of air moving towards the filter layers 15, 16.

In addition, having the outlet portions 26 of the ducts 25 provided with auxiliary outlet openings 35 at opposite locations with respect to the respective main outlet openings 31 allows the mixture of air and sterilizing agent to reach the corners of the box-like structure 10 of the filter assembly 6.

The increased mixing effect between the air and the sterilizing agent leads to a more homogeneous distribution of the sterilizing agent within any part of the filter assembly 6 and in particular of the filter layers 15, 16.

Plus, the improved mixing effect between the air and the sterilizing agent allows to reduce the time needed to obtain the desired sterilization effect of the filter unit 1.

Clearly, changes may be made to air filter unit 1 as described herein without, however, departing from the scope of protection as defined in the accompanying claims.

In particular, filter assembly 6 may comprise one single filter layer or more than two filter layers.

Moreover, each pre-filter 24 may be interposed between the respective blower 22 and the respective duct 25.

Furthermore, air filter unit 1 may comprise one single blower 22 connected to the filter assembly 6 through two ducts 25 and therefore generating two airflows F along such ducts 25.

Finally, air filter unit can be realized by comprising one single heating member 36 adapted to heat both airflows F.

The invention claimed is:

1. An air filter unit for removing contaminations from air, comprising:
   an airflow generating device configured to generate and direct at least one airflow from an air inlet to an air outlet;
   a filter disposed between the air inlet and the air outlet and including at least one filter layer for removing contaminations from the at least one airflow;
   a heater disposed upstream of the filter and configured to heat the at least one airflow directed towards the filter;
   an ejection device disposed upstream of the filter and configured to inject a sterilizing agent into the at least one airflow directed towards the filter; and
   a duct interposed between the air inlet and the filter and configured to feed the at least one airflow to the filter;
   a mixer configured to mix the at least one airflow and the sterilizing agent injected into the at least one airflow by the ejection device; and
   a distributor configured to uniformly distribute heat from the heater to at least one of the at least one airflow and the sterilizing agent,
   wherein the duct includes a volute outlet portion for conveying the at least one airflow to the filter,
   wherein the ejection device is arranged in the duct between the air inlet and the volute outlet portion, and
   wherein the mixer comprises the volute outlet portion.

2. The unit according to claim 1, wherein
   the ejection device is configured to inject the sterilizing agent transversally to the at least one airflow,
   the heater is arranged in the duct between the air inlet and the volute outlet portion, and
   the distributor comprises the volute outlet portion.

3. The unit according to claim 1, wherein the ejection device includes an ejection conduit projecting transversally from a lateral wall within the duct.

4. The unit according to claim 3, wherein the ejection conduit is inclined towards the filter.

5. The unit according to claim 3, wherein the ejection conduit includes at least one radial outlet hole having an axis transversal to the at least one airflow.

6. The unit according to claim 1, wherein the heater is arranged in the duct.

7. The unit according to claim 1, wherein the heater and the ejection device are adjacent to one another.

8. The unit according to claim 1, wherein the volute outlet portion of the duct opens into a chamber located adjacent to, and upstream of, the at least one filter layer with respect to the at least one airflow, and wherein the volute outlet portion defines a main outlet opening lying on a plane transversal to the at least one filter layer.

9. The unit according to claim 8, wherein the plane on which the main outlet opening lies is slanted with respect to the at least one filter layer and defines an acute angle with the at least one filter layer.

10. The unit according to claim 8, wherein the volute outlet portion of the duct includes an auxiliary outlet opening arranged within the chamber and opposite to the main outlet opening.

11. The unit according to claim 8, wherein the air inlet includes two air inlets, and the duct includes two ducts interposed between the respective air inlets and the respective filters and configured to feed two airflows to the filter, and wherein the volute outlet portions of the respective ducts are arranged at opposite sides of the chamber.

12. An air filter unit for removing contaminations from air, comprising:

an airflow generating device configured to generate and direct at least one airflow from an air inlet to an air outlet;

a filter disposed between the air inlet and the air outlet and including at least one filter layer for removing contaminations from the at least one airflow;

a heater disposed upstream of the filter and configured to heat the at least one airflow directed towards the filter;

an ejection device disposed upstream of the filter and configured to inject a sterilizing agent into the at least one airflow directed towards the filter; and a duct interposed between the air inlet and the filter and configured to feed the at least one airflow to the filter, wherein the duct includes an outlet portion for conveying the at least one airflow to the filter, and wherein the ejection device is arranged in the duct, wherein the outlet portion of the duct opens into a chamber located adjacent to, and upstream of, the at least one filter layer with respect to the at least one airflow, and wherein the outlet portion defines a main outlet opening lying on a plane transversal to the at least one filter layer, wherein the outlet portion of the duct includes an auxiliary outlet opening arranged within the chamber and opposite to the main outlet opening, and wherein the main outlet opening of the outlet portion of the duct is larger than the auxiliary outlet opening.

13. The unit according to claim 1 further comprising a deflector element arranged inside the duct and extending transversally to the at least one airflow, the deflector element configured to disrupt the at least one airflow.

14. The unit according to claim 13, wherein the deflector element is arranged upstream of the heater and the ejection device.

15. The unit according to claim 1, wherein the at least one filter layer includes two filter layers, wherein a first filter layer is disposed between the airflow generating device and the air outlet, and a second filter layer is disposed between the first filter layer and the air outlet.

16. An air filter unit for removing contaminations from air, comprising:

an airflow generating device configured to generate and direct at least one airflow from an air inlet to an air outlet;

a filter disposed between the air inlet and the air outlet and including at least one filter layer for removing contaminations from the at least one airflow;

a heater disposed upstream of the filter and configured to heat the at least one airflow directed towards the filter;

an ejection device disposed upstream of the filter and configured to inject a sterilizing agent into the at least one airflow directed towards the filter; and a duct interposed between the air inlet and the filter and configured to feed the at least one airflow to the filter, wherein the duct includes an outlet portion for conveying the at least one airflow to the filter, and wherein the ejection device is arranged in the duct, wherein the outlet portion of the duct opens into a chamber located adjacent to, and upstream of, the at least one filter layer with respect to the at least one airflow, and wherein the outlet portion defines a main outlet opening lying on a plane transversal to the at least one filter layer, wherein the air inlet includes two air inlets, and the duct includes two ducts interposed between the respective air inlets and the respective filters and configured to feed two airflows to the filter, and wherein the outlet portions of the respective ducts are arranged at opposite sides of the chamber, and wherein the main outlet openings of the respective ducts face respective staggered portions of an intermediate plane extending between the respective ducts and orthogonal to the filter.

17. An air filter unit for removing contaminations from air, comprising:

an airflow generating device configured to generate and direct at least one airflow from an air inlet to an air outlet;

a filter disposed between the air inlet and the air outlet and including at least one filter layer for removing contaminations from the at least one airflow;

a heater disposed upstream of the filter and configured to heat the at least one airflow directed towards the filter;

an ejection device disposed upstream of the filter and configured to inject a sterilizing agent into the at least one airflow directed towards the filter; and a duct interposed between the air inlet and the filter and configured to feed the at least one airflow to the filter;

a mixer configured to mix the at least one airflow and the sterilizing agent injected into the at least one airflow by the ejection device; and a distributor configured to uniformly distribute heat from the heater to at least one of the at least one airflow and the sterilizing agent, wherein the duct includes a volute outlet portion for conveying the at least one airflow to the filter, wherein the at least one filter layer includes two filter layers, wherein a first filter layer is disposed between the airflow generating device and the volute outlet portion, and a second filter layer is disposed between the first filter layer and the volute outlet portion, wherein the ejection device is arranged in the duct between the air inlet and the volute outlet portion, and wherein the mixer comprises the volute outlet portion.

18. The unit according to claim 17, wherein the ejection device is configured to inject the sterilizing agent transversally to the at least one airflow, the heater is arranged in the duct between the air inlet and the volute outlet portion, and the distributor comprises the volute outlet portion.

19. The unit according to claim 17, wherein the ejection device is configured to inject the sterilizing agent transversally to the at least one airflow, the heater is arranged upstream of the duct with respect to a direction of flow of the at least one airflow, and the distributor comprises the volute outlet portion.

20. An air filter unit for removing contaminations from air, comprising:

an airflow generating device configured to generate and direct at least one airflow from an air inlet to an air outlet;

a filter disposed between the air inlet and the air outlet and including at least one filter layer for removing contaminations from the at least one airflow;

a heater disposed upstream of the filter and configured to heat the at least one airflow directed towards the filter;

an ejection device disposed upstream of the filter and configured to inject a sterilizing agent into the at least one airflow directed towards the filter;

at least two ducts interposed between the air inlet and the filter and configured to feed turbulent airflows to the filter;

a mixer configured to mix the at least one airflow and the sterilizing agent injected into the turbulent airflows by the ejection device; and a distributor configured to uniformly distribute heat from the heater to at least one of the at least one airflow and the sterilizing agent, wherein the at least two ducts include volute outlet portions for conveying the turbulent airflows to the filter, wherein the at least one filter layer includes two filter layers, wherein a first filter layer is disposed between the airflow generating device and the volute outlet portions, and a second filter layer is disposed between the first filter layer and the volute outlet portions, and wherein the mixer comprises the volute outlet portions.

21. The unit according to claim 20, wherein the distributor comprises the volute outlet portions.

22. The unit according to claim 20, wherein the ejection device is configured to inject the sterilizing agent transversally to the turbulent airflows, the heater is arranged upstream of the duct with respect to a direction of flow of the turbulent airflows, and the distributor comprises the volute outlet portions.

\* \* \* \* \*